United States Patent [19]

Harttig et al.

[11] Patent Number: 5,679,311

[45] Date of Patent: Oct. 21, 1997

[54] SYSTEM FOR THE ANALYSIS OF SAMPLE LIQUIDS

[75] Inventors: Herbert Harttig, Altrip; Susanne Gentsch, Jever; Elmar Schmidt, Mannheim; Rudolf Schuessler, Lampertheim, all of Germany

[73] Assignee: Boehringer Mannheim GmbH, Mannheim, Germany

[21] Appl. No.: 748,916

[22] Filed: Nov. 13, 1996

Related U.S. Application Data

[62] Division of Ser. No. 282,149, Jul. 29, 1994, Pat. No. 5,609,823.

[30] Foreign Application Priority Data

Aug. 5, 1993 [DE] Germany .......... 43 26 339.9

[51] Int. Cl.⁶ .......... G01N 33/52; G01N 35/10; B65D 69/00
[52] U.S. Cl. .......... 422/102; 422/58; 422/66; 422/104; 436/44; 436/46; 221/210; 221/214
[58] Field of Search .......... 422/58, 63, 66, 422/102, 104; 436/43, 44, 46, 48, 174; 221/210, 214, 268

[56] References Cited

U.S. PATENT DOCUMENTS

| | | | |
|---|---|---|---|
| 3,526,480 | 9/1970 | Findl et al. | 422/66 |
| 3,918,910 | 11/1975 | Soya et al. | 422/66 |
| 3,932,133 | 1/1976 | Ishikawa | 422/66 |
| 4,218,421 | 8/1980 | Mack, Jr. et al. | 422/66 |
| 4,301,414 | 11/1981 | Hill et al. | 324/446 |
| 4,328,184 | 5/1982 | Kondo | 422/58 |
| 4,453,406 | 6/1984 | Spitzer | 73/422 R |
| 5,077,010 | 12/1991 | Ishizaka et al. | 422/56 |
| 5,096,828 | 3/1992 | Ishizaka et al. | 436/44 |
| 5,268,059 | 12/1993 | Olson | 156/584 |
| 5,400,699 | 3/1995 | Cailbault | 99/357 |

FOREIGN PATENT DOCUMENTS

| | | |
|---|---|---|
| 0585744 A1 | 3/1994 | European Pat. Off. . |
| 2096314 | 10/1982 | United Kingdom . |

OTHER PUBLICATIONS

Patent Abstracts of Japan, vol. 013, No. 073, Feb. 20, 1989 & JP–A–63 259469.

*Primary Examiner*—Long V. Le
*Attorney, Agent, or Firm*—Nikaido, Marmelstein, Murray & Oram LLP

[57] ABSTRACT

A storage container for analytical test elements includes a guide mechanism thereupon. The storage container holds a plurality of test elements attached to a tape, with each of the test elements including a test zone thereupon. The storage container is configured to expel individual test elements by passing the tape over the guide mechanism, thereby changing a direction of movement of the tape by the guide mechanism. This action detaches a test element from the tape.

8 Claims, 3 Drawing Sheets

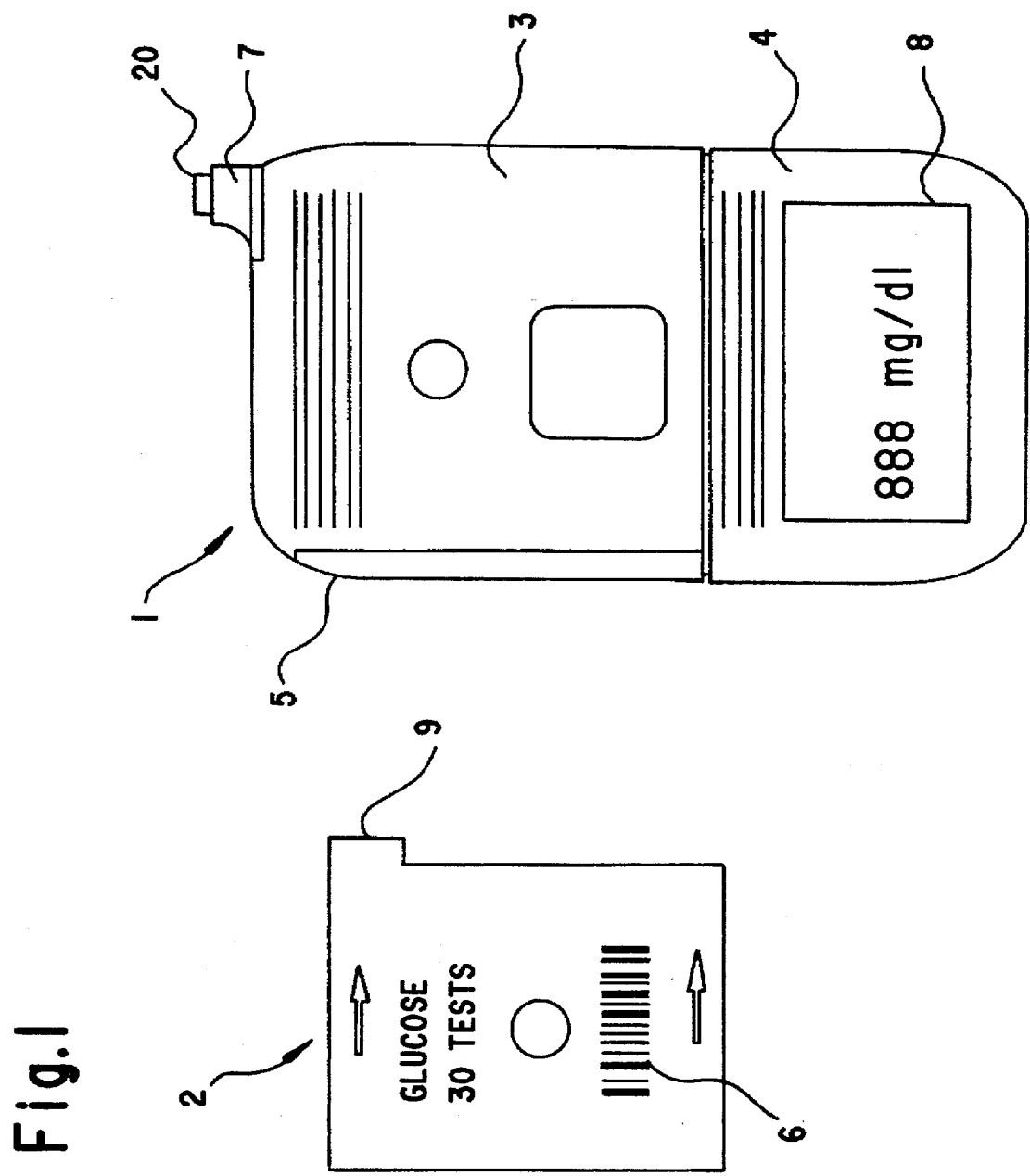

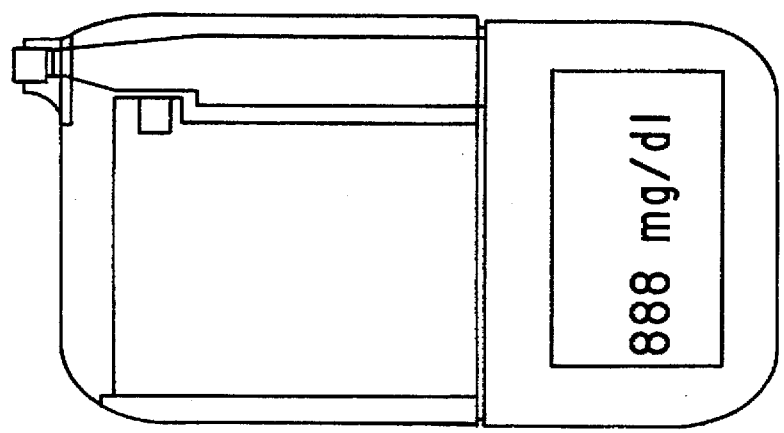
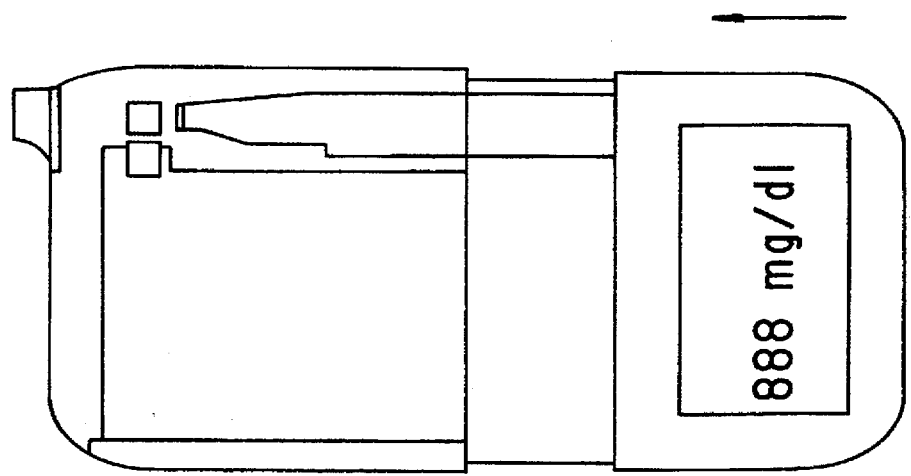
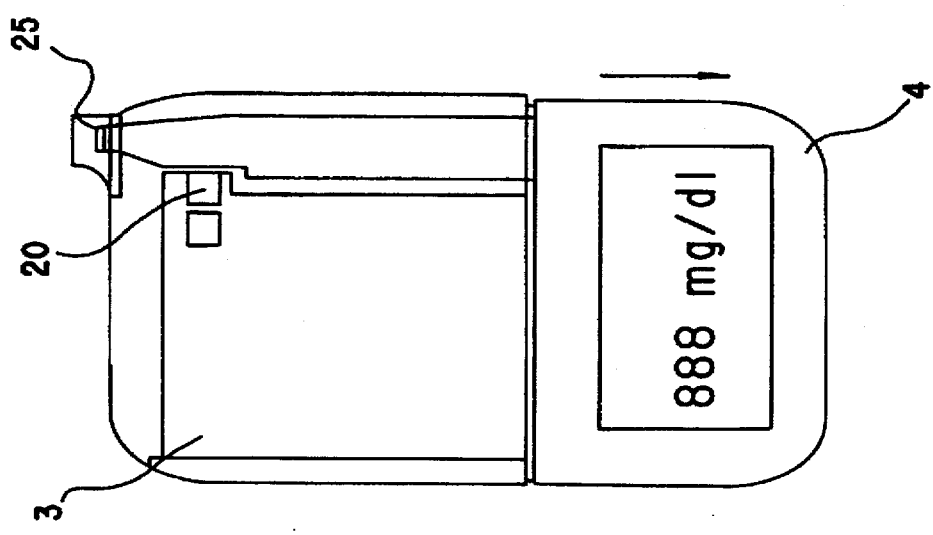

SYSTEM FOR THE ANALYSIS OF SAMPLE LIQUIDS

This is a division of application Ser. No. 08/282,149 filed Jul. 29, 1994, now U.S. Pat. No 5,609,823.

BACKGROUND OF THE INVENTION

1. Field of the Invention

The present invention concerns a system for the analysis of sample liquids comprising the elements: a measuring instrument with a source of radiation, radiation receiver, evaluation and display device, a storage container for holding test elements in which the test elements are arranged spirally and are individually sealed.

In addition the invention concerns a storage container with a spiral in its interior, a method for the analysis of sample liquids and an arrangement of test elements in which the test elements are connected by a tape.

2. Description of the Related Art

The invention lies within the field of analysis of sample liquids without reagent liquids like those which are used especially for the analysis of body fluids. Various systems for the determination of glucose in blood are known in the state of the art which attempt to achieve a simple and hygienic operation. Devices are described in the patent applications EP-A 0 373 629 and EP-A 0 373 413 which have a storage container for elements for sample application which enables several consecutive determinations of test substances. The elements for sample application have a membrane for separating cells and particles of blood serum. The concentration of a component is determined in the blood serum that passes through the membrane using an electronic sensor. In principle three different specific embodiments of the storage vessel for sample application are presented. In a first variant the elements are located on a disc which is rotated in order to move the elements in succession to the site intended for sample application. In a second specific embodiment strips stacked on top of one another, each of which carries a membrane for sample application, are located in a storage vessel from which they can be transported to the site of sample application. In a third variant membranes for sample application are on a film strip which is rolled up in a cylindrical storage vessel comparable to a photographic film. In each of the said variants the elements for sample application have no reagents that convert the concentration of a component of the sample liquid into a signal; sensors are therefore necessary that directly detect a component to be determined.

The described state of the art thus has the disadvantage that sensors are brought into direct contact with the blood serum that passes through the membrane. This can lead to a contamination of the sensor which can result in a falsification of the measured result and moreover leads to problems of hygiene when it is for example possible for viruses to penetrate the said membranes. For reasons of hygiene it is also disadvantageous in the described prior art that used elements for sample application remain in the system.

SUMMARY OF THE INVENTION

The object of the invention was therefore to provide a system for the analysis of sample liquids in which several test elements for carrying out the analysis are present in the system in such a way that they can be used consecutively without having to refill from outside for each determination. An object of the invention was also to create a system which meets hygienic requirements and which—through a longer stability of the test elements—also enables determinations at intervals of weeks with constant accuracy.

The said objects were achieved according to the invention by a system for the analysis of sample liquids which comprises a measuring instrument with a source of radiation, radiation receiver, evaluation and display device and in addition has a storage container for holding test elements in which the test elements are arranged spirally and are individually sealed and in the test elements of which a test zone is present on the front end of a transparent pin. The invention also encompasses a storage container in which the test elements are arranged spirally and a method for the analysis of sample liquids with a system according to the invention.

The test elements of the system according to the invention are located in an instrument that enables analyses to be carried out simply. This instrument has devices with which the test elements can be transported from the storage vessel to a site of sample application. This or further devices can also serve to transport test elements to a site of measurement. In a preferred specific embodiment of the system the site of sample application and site of measurement coincide, which simplifies the operation of the system since an additional transport process is not necessary. The said transport devices can also be used to eject a used test element from the system for which, however, additional devices can also be installed. In a preferred embodiment the test elements are transported from a storage container using a tape on which the test elements are lined up. The further transport of the test elements to the site of sample application or measurement is carried out with the aid of a slide that is also rigidly connected to the optical system.

Before use the test elements are located in a storage container. The present invention also concerns storage vessels for use in a system according to the invention that contains test elements arranged spirally. This storage container is preferably in the form of a box with a height of 3 to 20 mm. The basal surface of this box can be essentially rectangular and also round or rounded. The arrangement of the test elements can also be supported by a spiral passage within the storage vessel. The test elements can be transported from the system through a lateral opening. For protection against atmospheric humidity it is advantageous to market the storage container together with a desiccant heat-sealed in a polyethylene bag lined with aluminium.

The spiral arrangement of the test elements enables numerous test elements to be arranged in a space-saving manner in the storage vessel. In this way it is also possible to remove test elements consecutively whereby the test elements are removed from the system in their predetermined orientation. This arrangement also prevents the test elements from snagging.

The storage container can be manufactured from materials that can be made into the necessary shape and have an adequate mechanical stability. Materials which come into consideration are for example cardboard, metals such as aluminium, tin plate, brass etc. and preferably plastics such as polyethylene, polypropylene, polymethylmethacrylate and polystyrene. The storage containers can be manufactured using the processes known in the state of the art for the respective materials. The storage container preferably bears a code strip on which batch-specific informations are present in a machine-readable form. Magnetic codes, bar codes and also machine-readable plain text come into consideration for this. When the storage container is inserted into the appropriate compartment or drawer of the measuring instrument, the code on the magazine is automatically read by a reading device located in the instrument.

Test elements according to the invention have a transparent, essentially cylindrical, plastic pin which has a diameter of about 2 to 6 mm and a length of about 2 to 15 mm. The plastic pin is surrounded by a sheath in such a way that the front ends remain free. Basically any material that is permeable to light is suitable as a material for the transparent pin. Optically clear plastics have proven to be particularly satisfactorily. Polymethylmethacrylate and polycarbonate are preferred. A corresponding test element is the subject matter of the German Patent Application file number P 4227678.0 and the European Patent Application EP-A-0 585 744.

The sheath which surrounds the transparent pin can also be a plastic such as polyethylene, polypropylene or polyvinylidene fluoride. It has turned out to be advantageous when the refractive indices of the transparent pin and sheath are such that the condition for total reflection is fulfilled for light entering the transparent pin. Possible combinations for the pin/sheath are polycarbonate/polyethylene and polymethylmethacrylate/polyvinylidene fluoride. The transparent pin can also be surrounded by a metal coating, for example of aluminium deposited by evaporation. The metal coating can in turn be surrounded by a plastic sheath. The sheath enclosing the plastic pin is preferably impervious to gas and liquid. The sheath preferably protrudes beyond the front ends of the plastic pin.

A reagent layer is applied to one of the front ends of the plastic pin that produces an optically detectable signal by reaction with an analyte to be determined. Further layers can be applied to the reagent layer which for example enable the separation of cells. The composition of reagent and auxiliary layers can be derived from the prior art for test strips. In a preferred embodiment a metal coating produced by vapourization is located above the reagent and auxiliary layers. This metal coating has the function of shielding against ambient light and against the red colour of the blood. At a thickness of ca. 70 μm such a metal layer, which is preferably composed of aluminium, is adequately light-tight and sufficiently permeable to sample liquids. Detailed instructions for the metallization of a reagent layer are to be found in the German Patent Application with the file number P 4227665.9 and the European Patent Application EP-A 0 584 721.

The side of the test element on which the reagent is located can be sealed onto an essentially water-impermeable foil, e.g. an aluminium foil or an aluminium laminate, using the protruding sheath surface of the test element. This can for example be carried out by melting on or glueing on. An advantage of this embodiment is that the reagent is sealed off to the environment in a vapour-tight manner which ensures the stability of each test element over weeks. If the seal on a test element is removed, then the seal of the other test elements remains intact. This type of sealing is denoted individual sealing. It is possible according to the invention to attach the test elements to the tape or foil using other sides or sites. In cases in which the tape does not have the function of a seal, the site of attachment can be chosen relatively freely.

The sealing can be carried out in such a way that the sealed test elements are present separately. However, it is preferable to seal two or several test elements onto different sites on the water-impermeable foil so that the test elements are mechanically connected together. If the foil is in the form of a tape, the test elements can then be coiled up using this tape. The test elements can also be transported by this tape.

The tape with the individual sealed-on tests is preferably inserted spirally into a magazine. In order to enable the shortest possible transport path for the test elements in the measuring instrument, their orientation is preferably selected so that the tape lies on the outer side of the spiral. Incorporation of a supporting spiral in the interior of the storage container, enables the tape with the sealed-on test elements to be pulled out without snagging.

A leader of the tape on which the test elements are located is attached to the core of a spool. This spool core is rotated by a mechanism e.g. a gear wheel. This results in a tape being pulled out from the magazine together with the test elements.

When a test element is pulled out this is unsealed by the tape being pulled off. This is preferably achieved by changing the direction of movement of the tape by a guide mechanism. One possibility is to position a roller or edge at the exit opening of the storage vessel over which the tape runs.

An unsealed test element is brought into a sample application position. When the test element is transported to the sample application position it is preferably pushed into a seal which embraces the sheath of the test element. In this way sample liquid is prevented from penetrating into the interior of the instrument. It is also advantageous to protect the socket that holds the test element during sample application against penetration of dust, spray water etc. in its empty state by means of a flap. Such a flap can be pushed up by the insertion of the test element.

The measurement of a signal that is characteristic for the concentration of a component to be determined takes place at the end of the test element that faces away from the reagent. Their radiation and signal reading are preferably both carried out perpendicular to the lower face of the transparent pin. Cross-talk from transmitter to receiver can be reduced by a screen placed between them. This arrangement combines the possibilities of small structural size and relatively large tolerances for spacing. A transmitter for use in a system according to the invention preferably emits electromagnetic radiation in the optical part of the spectrum. Due to their small size and power consumption, light-emitting semiconducting diodes have proven to be particularly suitable for this purpose. Diodes in the red and infrared range are used advantageously for the remission measurement that is preferred according to the invention.

The receiver receives radiation that is irradiated from the side of the reagent layer facing the transmitter and receiver. The radiation frequencies received by the receiver preferably essentially correspond to those that are emitted by the transmitter. However, it is also possible that the radiation emitted by the transmitter and that received by the receiver differ in their frequency range if for example fluorescent processes take place in the reagent layer. Semiconducting components are preferably used as a receiver such as photodiodes or phototransistors; however, other receivers for electromagnetic radiation known in the state of the art can also be used.

The invention also encompasses a method for the analysis of sample liquids using a system with an arrangement of test elements that are linked together by a tape and are located in a storage container comprising the steps: transporting a test element by means of a tape out of the storage vessel, opening the seal of the test element by pulling off the tape from the test element so that a test zone of the test element becomes accessible, applying a sample liquid to the test element, carrying out the measurement process while irradiating the test element and measuring the reflected or transmitted radiation, calculating an analytical result from the measurement, ejecting the used test element from the system.

Transport of a test element from the storage container to the site of sample application can be achieved in that an unused test element on the tape that links the test elements is pulled out by a mechanism and it is subsequently pushed to the site of sample application. The withdrawal is for example achieved by turning the spool core of the storage container or by pulling the tape that links the test elements. Preferably a tape in the form of a foil that seals the test elements is pulled over an edge or roller of small diameter in such a way that the foil is thereby detached from the test element and this is then ready for application of the sample liquid. However, it is also possible that the detachment of a test element and thus the opening of the seal is carried out manually. The transport of a test element to the site of sample application is preferably carried out mechanically. This transport process can—like the withdrawal process from the storage container—be linked to the opening of the test element seal. The application of a sample liquid to the test element is usually carried out manually whereby the test element is preferably present at an exposed site of the system so that a contamination of the system is prevented to a high degree.

The site of sample application and the site of measurement can be different in a system according to the invention so that transport of the test element is necessary.

Transport of the test element loaded with the sample liquid to the site of measurement is preferably carried out mechanically. An arrangement is particularly preferred in which the measurement is carried out directly at the position of sample application. The measurement can for example be started by the sample application by carrying out periodic measurements when the instrument is switched on that allow detection of the sample application. Measurement of the radiation remitted from the reagent layer is preferably subsequently carried out after a period of time has elapsed that is dependent on the test elements used and on the analysis to be carried out. It is also possible to carry out measurements at intervals and to store the change of the measured signal with time. Using such a process it is possible to determine the optimal time for calculation of the analytical result as well as the kinetics of the detection reaction.

The calculation of the analytical result from the measurement can be carried out with methods of data processing known in the state of the art. Allocations that enable a concentration to be determined from the measured signal can be present stored in the system. Preferably data are present that enable a calibration of the measurement for the test elements present in the storage container. These data may be already stored on the storage vessel in the variants that have already been described or they may be present separately. A linking of data for the test elements used in each case and data stored permanently in the system is particularly preferred for an evaluation of the measurement.

The determined analytical result can be displayed to the user on one of the displays known in the state of the art. It is also possible to display preceding analytical results with accompanying data, e.g. the date, so that the user can recognize a change in the analytical results. This is particularly advantageous in the field of glucose determination since the patient can monitor his glucose level in this manner.

An important characteristic of the system according to the invention is the ejection of used test elements after the measurement has been carried out. The ejection can be carried manually or preferably mechanically e.g. by moving the test element over a mechanical resistance with a slide that has transported it to the site of measurement.

A system according to the invention offers the user some advantages over conventional systems. The combination of a storage container with a measurement instrument enables numerous analyses to be carried out without the necessity for feeding in individual test elements from outside. The operation of a system according to the invention is also simplified by the fact that the transport and positioning of the test elements can be predetermined by devices in the system so that operating errors are reduced to a minimum. Ejection of used test elements meets hygienic requirements and reduces the risk of contaminating the instrument which could among others lead to erroneous measurements. The transport tape according to the invention combines, in a simple and effective manner, the individual sealing of the test elements and their transport which simplifies the working of the instrument. An individual sealing of the test element according to the invention enables analytical determinations to be carried out with the system over a period of weeks with the same filling of the storage container and with constant accuracy.

BRIEF DESCRIPTION OF THE DRAWINGS

A system according to the invention is characterized in more detail by the following figures wherein:

FIG. 1: illustrates an instrument for the determination of glucose and storage container for test elements utilizing the present invention.

FIGS. 4A, 4B and 4C illustrate process steps for the transport of a test element from the storage container to the site of sample application.

DETAILED DESCRIPTION OF THE PREFERRED EMBODIMENTS

Figure 2A:
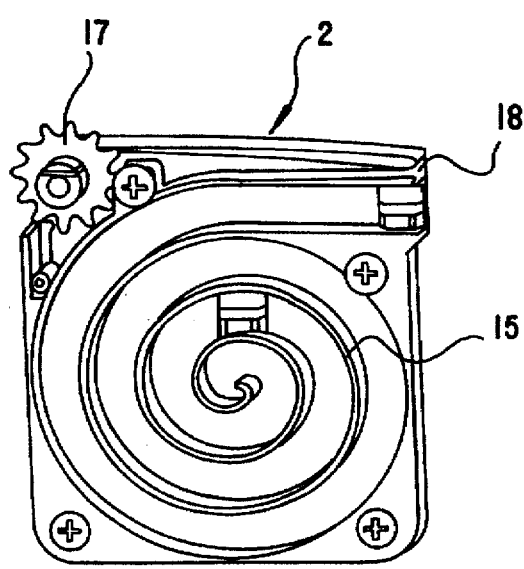
FIGS. 2a and 2b illustrate storage containers for test elements.

FIG. 1 shows an instrument (1) for the determination of glucose in blood and an accompanying storage container or storage vessel (2) for test elements. The instrument (1) has a two-part housing with an upper part (3) and a lower part (4). A drawer (5) is located at the side of the instrument in which the storage container (2) can be inserted. On insertion the bar code (6) on the upper side of the storage container (2) is read by a bar code reader present in the instrument (1). The data stored in the form of a bar code (6) relate to the expiry date of the test elements and batch-specific informations for calibration of the instrument (1). A protruding cone (7) is located on the instrument which serves to receive a test element (20) during sample application. This design enables the instrument to be directed to a drop of blood similar to a pen without other parts of the instrument coming into contact with blood. A liquid crystal display (8) is located on the top of the instrument (1) to display the analytical results.

Figure 2B:
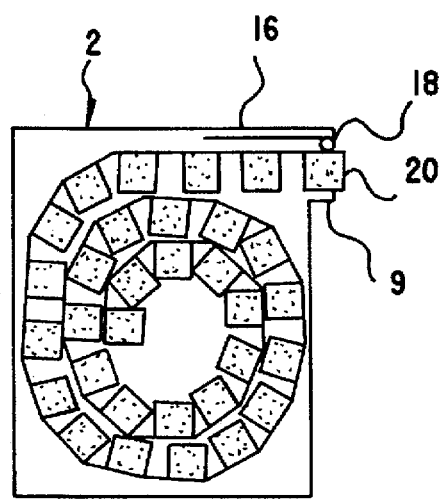

FIG. 2 shows two schematic representations of storage containers (2) for test elements (20). FIG. 2A shows a cross-section parallel to the top of the storage container. A spiral (15) in the interior of the storage container stabilizes a spiral coil of test elements as shown in FIG. 2B. The tape (16) is also shown which serves to mechanically link the test elements as well as to seal them. In this particular case an aluminium foil was used as the tape (16). The tape (16) is threaded into the core of the spool (17). When the core of the spool (17) is turned, the tape (16) is pulled over a roller (18) of small diameter which transports the arrangement of test elements towards the opening (9) of the storage container (2) and detaches the tape (16) from the test element (20) that passes through the opening (9) of the storage container.

Figure 3:
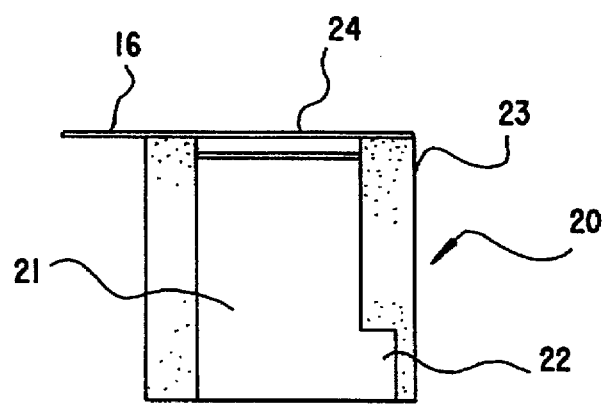
FIG. 3 illustrates a test element.

FIG. 3 shows an individual test element (20) in a sealed form. The transparent pin (21) is composed of polycarbonate and has a fin (22) which is formed during injection moulding of the pin. This fin (22) is of essential importance for the function according to the invention of the transparent pin (21) since it ensures that imperfections in the structure of the plastic due to the manufacturing process are shifted into this region and are thus kept out of the light path. The transparent pin (21) is surrounded by a sheath (23) of polyethylene which protrudes from the transparent pin (21) on the side facing the tape (16). Since the refractive indices of polycarbonate and polyethylene are substantially different, the condition for total reflection is fulfilled at the interface. A test zone (24) is located on the transparent pin (21) on which the sample liquid is applied. The test zone (24) and the sheath surface of the transparent pin (21) are coated with a thin aluminium layer of about 70 nm. The space above the test zone is sealed off from the surroundings in a water-vapour-tight manner by the aluminium foil (16). The reagent layer of the test zone (24) does not therefore come into direct contact with atmospheric humidity.

FIG. 4 shows a diagram of the transport of a test element (20) from the storage container (2) to the site of sample application. Firstly the lower part (4) and the upper part (3) are pulled apart by about 30 mm (FIG. 4A). The instrument is switched on after a displacement of a few millimeters. The display device can show the number of stored test elements, the last measured value or a prompt for an action. In this position earlier results can be called up from the memory and displayed by operating a memory key. After sliding a distance of ca. 10 mm a resting point is passed that blocks a reversal of the movement. From this point the entire analytical process has to be carried through.

This opening movement also moves the optical system (25) which is located on the upper face of a pin (26) along the magazine to such an extent that the upper edge of the optical system (25) is below the lower edge of the test elements (FIG. 4B).

After the resting point, the spool core (17) of the storage container (2) is rotated by engagement of a gear rack and by this means the tape (16) is wound on to such an extent that a test element is pulled out of the magazine. In this process the test element is freed of its seal by the roller (18).

The tape winding is disengaged at the reversal point of the movement.

When the instrument is subsequently pushed together, the exposed test element is pushed into the cone (7) by the top edge of the optical measurement system (FIG. 4C).

The cone (7) is designed in such a way that a dust guard folds away or is pushed aside when the test element is inserted. When the sample application position is reached, the upper end of the test element (20) protrudes about 2.0 to 2.5 mm from the instrument. Due to the cone (7) the surface of the test element can stand out 8 to 12 mm from the main contour of the instrument (1).

When it is pushed together the next test element that is still sealed is subsequently pushed back by up to 3 mm into a defined starting position while unwinding the aluminium foil that is already wound from the spool core. This ensures that no problems of positioning occur due to slightly different winding distances with increasing spool diameters.

When the measuring position is reached that is identical with the sample application position, a blank measurement is carried out with a delay of a few tenths of a second. A prompt to apply a sample appears on the liquid crystal display (8).

A blood drop of a few µl suffices as a sample. Selection of a hydrophobic plastic such as polypropylene (PP) or polyethylene (PE) for the sheath of the test element and PP or polyvinylidene fluoride (PVDF) for the cone (7) results in the blood not spreading beyond the reagent layer (24) onto the instrument. On the contrary a large supply of sample forms a small spherical drop on the detection zone whereas the larger part remains on the skin of the patient. If, in the case of a patient who is bleeding strongly, blood drops in free fall onto the sample application site, then the hydrophobic materials reduce the risk of blood penetrating into the instrument and contaminating it. The contamination safety can be further increased by a tight fitting and, if desired, a sealing washer on the cone (7). Should a cleaning become necessary, this can be facilitated by a removable version of the cone (7).

The sample application can be detected by the instrument itself by a change in the optical properties of the test element (20). The display of the measured value can be accompanied by an acoustic signal.

30 to 60 seconds after displaying the measured result, the user is prompted by the display and an acoustic signal to eject the used test element. For this the housing is pushed together by a further 2.5 mm after overcoming a barrier. Return to the starting state is achieved by a spring.

The instrument is switched off at the same time as the ejection. If no function is operated while the instrument is switched on, then an acoustic warning occurs after a waiting period of ca. 3 minutes and afterwards an automatic switch-off. A new start can only be carried out after the used test element has been ejected.

The German and European Patent Application identified on pages 1, 5 and 6 are hereby incorporated by reference for the respective disclosures therein.

Pin 26 of FIG. 4A, B and C has an optical system 25 located thereon. Optical system 25 includes a radiation source and a radiation receiver, such as the system shown in U.S. Pat. No. 4,685,059, the disclosure of which is hereby incorporated by reference for the teachings of such an optical system therein.

List of reference symbols (1) instrument
(2) storage container
(3) upper part of the instrument
(4) lower part of the instrument
(5) drawer
(6) bar code
(7) cone
(8) liquid crystal display
(9) opening of the storage container
(10) —
(14) —
(15) spiral
(16) tape
(17) spool core
(18) roller
(19) —

(20) test element
(21) transparent pin
(22) fin
(23) sheath
(24) test zone
(25) optical system
(26) pin

We claim:

1. A storage container for analytical test elements, said storage container comprising: a guide mechanism and a housing for holding a plurality of test elements attached to a tape, with each of the test elements comprising a test zone, wherein said storage container is configured to expel individual test elements of the plurality of test elements by passing said tape over said guide mechanism thereby changing a direction of movement of the tape by the guide mechanism and detaching a test element from said tape.

2. The storage container as recited in claim 1, wherein each of said test zones is individually sealed by said tape.

3. The storage container as recited in claim 1, wherein each test element includes a transparent pin having a front side on which is a test zone.

4. The storage container as recited in claim 1, wherein the plurality of test elements are linked together by said tape, and the storage container includes transport means for transporting the tape through the storage container by winding the tape onto a spool core and for detaching a test element emerging from the storage container from the tape by passing the tape over the guide mechanism.

5. The storage container as recited in claim 1, wherein said guide mechanism comprises a roller.

6. A storage container as recited in claim 1, wherein said guide mechanism comprises an edge.

7. A storage container as recited in claim 1, wherein said storage container including an interior spiral which stabilizes a spiral arrangement of the plurality of test elements, wherein the individual test elements are for the analysis of sample liquids.

8. A storage container as recited in claim 1, wherein each test zone is configured to have a sample liquid applied thereto, each test element also including a sheath, with the tape being fixed onto each sheath so that each test zone is protected against entry of atmospheric humidity.

* * * * *